(12) United States Patent
Scott et al.

(10) Patent No.: US 10,398,581 B2
(45) Date of Patent: *Sep. 3, 2019

(54) METHOD FOR PERFORMING A GASTRECTOMY

(71) Applicant: Freehold Surgical, Inc., New Hope, PA (US)

(72) Inventors: J. Stephen Scott, New Hope, PA (US); Roger de la Torre, New Hope, PA (US)

(73) Assignee: Freehold Surgical, Inc., New Hope, PA (US)

( * ) Notice: Subject to any disclaimer, the term of this patent is extended or adjusted under 35 U.S.C. 154(b) by 331 days.

This patent is subject to a terminal disclaimer.

(21) Appl. No.: 15/478,643

(22) Filed: Apr. 4, 2017

(65) Prior Publication Data

US 2017/0202694 A1    Jul. 20, 2017

Related U.S. Application Data

(63) Continuation of application No. 15/064,527, filed on Mar. 8, 2016, now Pat. No. 9,615,952, which is a continuation of application No. 14/009,842, filed as application No. PCT/US2012/032138 on Apr. 4, 2012, now abandoned.

(60) Provisional application No. 61/471,454, filed on Apr. 4, 2011.

(51) Int. Cl.
| | | |
|---|---|---|
| *A61F 5/00* | (2006.01) | |
| *A61B 17/30* | (2006.01) | |
| *A61B 90/00* | (2016.01) | |
| *A61B 17/00* | (2006.01) | |
| *A61M 25/04* | (2006.01) | |

(52) U.S. Cl.
CPC ............ *A61F 5/0086* (2013.01); *A61B 17/30* (2013.01); *A61B 2017/00818* (2013.01); *A61B 2017/306* (2013.01); *A61B 2090/395* (2016.02); *A61M 25/04* (2013.01)

(58) Field of Classification Search
CPC .... A61F 5/0083; A61F 5/0086; A61F 5/0076; A61F 5/0079; A61F 5/0036; A61F 2/04; A61B 17/30; A61B 17/0469; A61B 17/1114; A61B 17/221; A61B 2090/395; A61B 2017/306; A61M 25/04
See application file for complete search history.

(56) References Cited

U.S. PATENT DOCUMENTS

| | | | |
|---|---|---|---|
| 7,220,237 B2 * | 5/2007 | Gannoe | ............... A61B 17/072 128/898 |
| 9,615,952 B2 * | 4/2017 | Scott | ..................... A61F 5/0086 |
| 2008/0275473 A1 * | 11/2008 | Filipi | ................. A61B 17/0469 606/145 |
| 2010/0114125 A1 | 5/2010 | Albrecht et al. | |
| 2011/0257750 A1 | 10/2011 | Waldrep | |

* cited by examiner

*Primary Examiner* — Philip R Wiest
(74) *Attorney, Agent, or Firm* — K David Crockett, Esq.; Crockett & Crockett, PC (57) ABSTRACT

A method for performing a gastrectomy (stomach reduction surgery).

11 Claims, 7 Drawing Sheets

METHOD FOR PERFORMING A GASTRECTOMY

This application is a continuation of U.S. application Ser. No. 15/064,527, filed Mar. 8, 2016, now U.S. Pat. No. 9,651,952, which is a continuation of U.S. application Ser. No. 14/009,842, filed Oct. 4, 2013, abandoned, which is a national stage of PCT Application PCT/US2012/032138, filed Apr. 4, 2012, which claims priority to U.S. provisional application 61/471,454, filed on Apr. 4, 2011.

BACKGROUND OF THE INVENTION

The present invention pertains to an apparatus that is positioned in a hollow viscus organ and functions as a template for creating a lumen of a desired shape and size in the organ from the tissue of the organ, and the method of using the apparatus in creating the lumen.

SUMMARY

The apparatus of the invention is employed in creating a lumen of a desired shape and size in a hollow viscus organ from tissue of the organ. In particular, the present invention is employed in creating a tubular gastric sleeve from the tissue of a patient's stomach.

The apparatus is comprised of an elongate, flexible tube having opposite proximal and distal ends. The tube has several lumens or pathways that extend through the interior of the tube between the proximal and distal ends of the tube.

A directional, steerable feature extends through one of the lumens of the tube. The directional, steerable feature is manually operable at the tube proximal end to direct and steer the tube distal end in different directions relative to the length of the tube.

An anchor feature is provided at the tube distal end and is manually operable from the tube proximal end. The anchor feature selectively anchors or secures the tube distal end to tissue of a hollow viscus organ. In particular, the anchor feature can be selectively operated to secure the tube distal end in the beginning of the small intestine or duodenum of a patient.

An exterior surface dimension adjustable feature is provided adjacent the tube distal end. The adjustable feature is also manually operable at the tube proximal end. The adjustable feature can be selectively enlarged and reduced in shape configuration and circumferential dimensions. When enlarged, the exterior surface of the adjustable feature has its largest circumferential dimension at the end of the adjustable feature that is adjacent the tube distal end. From this end of the enlarged adjustable feature the circumferential dimension of the feature gradually decreases as the adjustable feature extends toward the tube proximal end.

A suction communication feature is provided along at least a portion of the tube length. The suction feature is also operable at the tube proximal end. Manual operation of the suction feature supplies suction pressure along at least a portion of the tube length that draws the tissue of the hollow viscus organ toward the exterior surface of the tube.

In use of the apparatus the tube distal end is first inserted through the patient's esophagus and then into the patient's stomach. The anchor feature at the tube distal end is guided from the stomach interior past the patient's pyloric valve and into the beginning of the small intestine or duodenum. The anchor feature is then operated to secure the tube distal end in its position. The length of the tube is then manually pulled from the proximal end to position the tube, and in particular the exterior surface dimension adjustable feature along the lesser curvature of the stomach and adjacent the stomach incisura. The exterior surface dimension adjustable feature is then enlarged. The suction communication feature is then operated, causing portions of the stomach wall to be drawn to and wrapped around the exterior surface dimension adjustable feature. The position of the adjustable feature along the stomach lesser curvature is then demarcated on the stomach exterior. Opposing portions of the stomach wall are then affixed together along the side portion of the enlarged dimension adjustable feature that is opposite the stomach lesser curvature, thereby creating a tubular gastric sleeve from the patient's stomach. The exterior surface dimension adjustable feature is then reduced in size, and the anchor feature is disengaged from the stomach. The apparatus is then removed from the patient's stomach leaving the gastric sleeve. The gastric sleeve will then function as a new gastric reservoir with an interior configuration that is without any significant, limiting constriction in the sleeve interior configuration in the area of the stomach incisura or other tenuous area of the reservoir after the apparatus has been removed.

DESCRIPTION OF THE DRAWINGS

Further features of the apparatus and its method of use are set forth in the following detailed description of the apparatus and method and in the drawing figures.

DESCRIPTION OF THE APPARATUS OF THE INVENTION AND ITS METHOD OF USE

The apparatus of the invention 12 is designed for use in surgical procedures in creating a lumen of a desired shape and size in a hollow viscus organ from the tissue of the organ. In one example of the method of using the apparatus disclosed herein, the apparatus is designed to be introduced through the esophagus of a human patient and into the patient's stomach. The apparatus is then positioned along the lesser curvature of the stomach and is used as a template or guide in creating a lumen of a desired shape and size in the stomach from stomach tissue wrapped around the apparatus. The apparatus 12 is therefore constructed of biocompatible materials typically employed in the constructions of surgery devices.

Although the apparatus 12 of the invention and its method of use are described herein as creating a lumen of a desired shape and size in the stomach from the tissue of the stomach, it should be understood that the apparatus 12 of the invention is designed to be used as a template or guide in creating a lumen of a desired shape and size in a hollow viscus organ, not necessarily the stomach.

The apparatus 12 is basically constructed as a bougie having an elongate flexible tube 14 with opposite proximal 16 and distal 18 ends. A plurality of separate bores or lumens represented by dashed lines 20 in FIG. 1 extend through the interior of the tube 14 from the tube proximal end 16 toward the tube distal end 18. The lumens provide separate paths of communication through the interior of the tube 14 that communicate a plurality of manually operable controls 22 at the tube proximal end 16 with a plurality of features of the apparatus 12 that are positioned along portions of the tube length adjacent the tube distal end 18.

Figure 1:
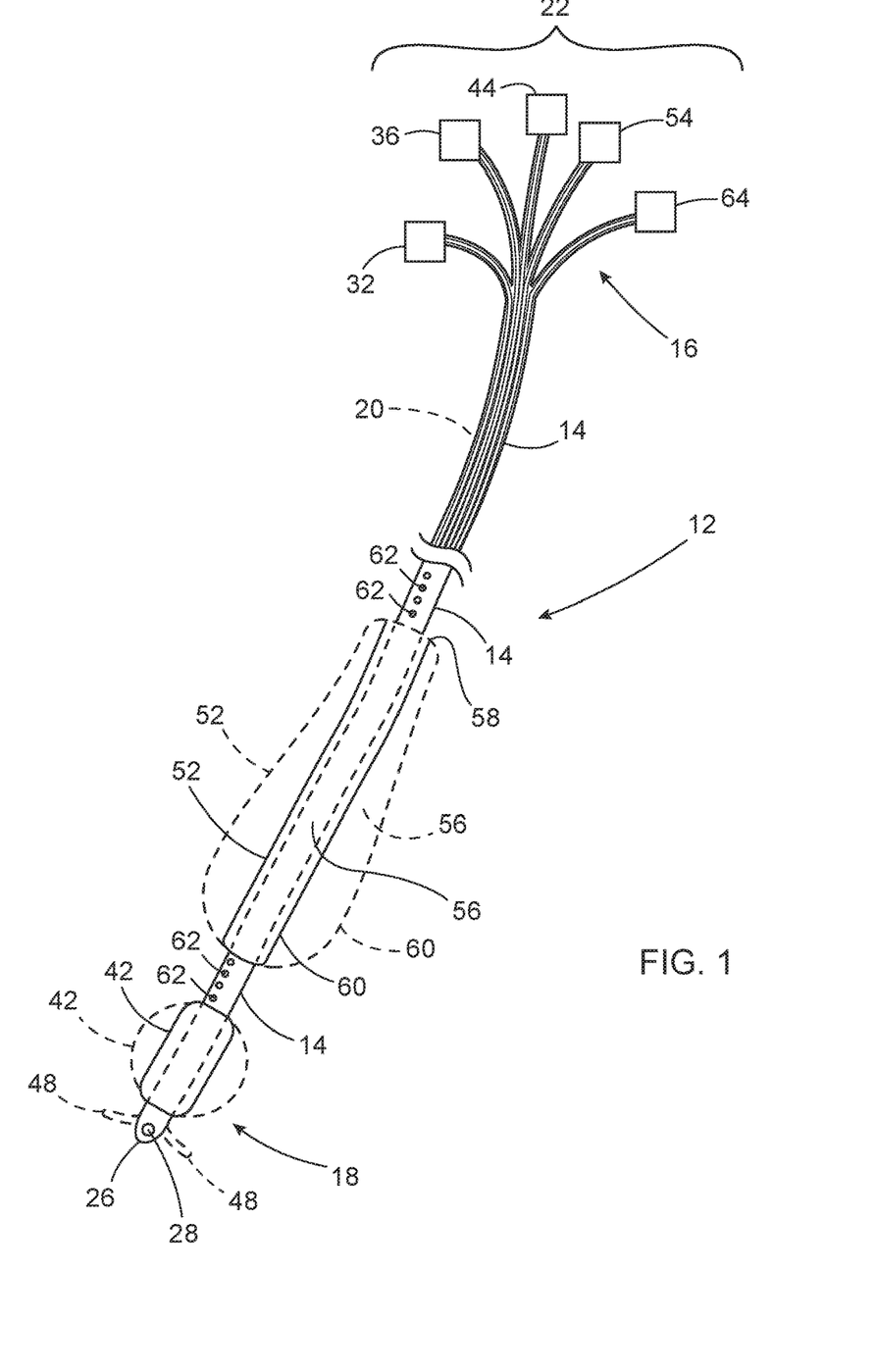
FIG. 1 is a representation of one embodiment of the apparatus of the invention.

The extreme distal end of the apparatus tube length is formed as a blunt tip 26 having a smooth exterior surface. This enables the distal end tip 26 to easily pass over or through body tissue without causing damage to the tissue. If desired, an illumination light and/or endoscope opening 28 could be provided in the distal end tip 26 of the tube. The light and/or endoscope would be connected by any known appropriate communication means through one of the lumens 20 extending through the length of the tube 14 with a manually operable control 32 provided for the light or endoscope at the tube 14 proximal end 16. In this manner, illumination light could be provided at the tube distal end tip 26. This enables the location of the tip 26 in the stomach to be identified through the stomach wall from the abdominal cavity. Additionally, an endoscope visual image could be provided at the tube distal end tip.

The apparatus tube 14 is also provided with a directional or steerable feature that extends from the distal end 18 through one of the lumens 20 to a manually operable control 36 of the feature at the tube proximal end 16. Any conventional or known directional or steerable feature could be employed in the construction of the apparatus 12 for this purpose. The directional/steerable feature would be operable at the proximal end 16 of the tube 14 to direct and steer the distal end 18 of the tube in different directions relative to the length of the tube 14. Examples of known directional/steerable features include those that employ wires that extend along different sides of the tube length that are pulled in tension to curve and direct the different sides of the tube length. Additionally, shape memory wires or other equivalent means could be employed as the directional/steerable feature of the apparatus 12.

The apparatus 12 is also provided with an anchor feature 42 at the tube distal end 18. In the embodiment of the apparatus 12 shown in FIG. 1, the anchor feature 42 is an inflatable balloon that communicates through one of the lumens 20 with a control 44 at the tube proximal end 16. The balloon anchor feature 42 is shown in solid lines in its deflated condition in FIG. 1, and in dashed lines in its inflated condition in FIG. 1. The manually operable control 44 provided at the tube length proximal end 16 controls the selective inflation and deflation of the balloon 42. In its deflated condition the balloon 42 is dimensioned to enable it to be inserted through the esophagus and into the stomach interior and from the stomach interior past the pyloric valve or sphincter and into the beginning of the small intestine or duodenum. With the balloon 42 so positioned, inflating the balloon 42 anchors the distal end portion 18 of the apparatus 12 in the duodenum. In this manner, the apparatus distal end 18 is securely anchored to the stomach tissue. In addition, the anchor feature 42 could be provided with an illuminating light that is controllable at the manual control 44. The anchor feature light would enable identifying the location of the anchor feature inside the stomach by viewing the light through the stomach well from inside the abdominal cavity.

In different embodiments of the apparatus 12, the balloon anchor feature 42 could be replaced with other equivalent types of anchors. For example, the balloon anchor feature 24 could be replaced with selectively extendable hooks or prongs 48 shown in dash lines in FIG. 1 that would also function to anchor the apparatus distal end 18 to the stomach tissue.

An exterior surface dimension adjustable feature 52 is also provided on the apparatus 12 along a portion of the tube 14. As shown in FIG. 1, the exterior surface adjustable feature 52 extends completely around the tube and along a significant portion of the tube 14 length adjacent the distal end 19 of the tube, but is spaced along the tube length and is separate from the anchor feature 42. The exterior surface adjustable feature 52 communicates through one of the lumens 20 with a manual control 54 provided for the feature at the tube proximal end 16. The control 54 is manually operated to selectively move the adjustable feature 52 between a retracted condition shown in solid lines in FIG. 1 and an extended or enlarged condition shown in dashed lines in FIG. 1. In the retracted condition the circumferential dimension of the adjustable feature 52 enables insertion of the feature through the esophagus of a patient and into the stomach of the patient. When manually operated to move to its enlarged condition in dashed lines in FIG. 1, the exterior surface 56 of the adjustable feature 52 has a shape configuration and circumferential dimensions along the length of the feature that enable it to be used as a template in creating a lumen of a desired shape and size in a hollow viscus organ from the tissue of the organ. In the example of FIG. 1, the adjustable feature 52 is used as a template for creating a lumen of a desired shape and size in the stomach tissue surrounding the adjustable feature 52 in performing the desired method of the invention that will be later described. One example of the desired shape configuration and circumferential dimensions of the exterior surface 56 of the adjustable feature 52 in its enlarged condition is shown in dashed lines in FIG. 1. The adjustable feature has a generally annular cross-section configuration defined by the circular cross-section of the tube 14 at its center and the exterior surface 56 of the adjustable feature 52. The exterior surface 56 extends around an interior volume of the adjustable feature 52 with the tube 14 at the center of the volume. The length of the adjustable feature 52 extends from a proximal end 58 of the exterior surface 56 to a distal end 60 of the exterior surface. As seen in FIG. 1, the circumferential dimension of the enlarged exterior surface 56 increases as it extends from adjacent the proximal end 58 to adjacent the distal end 60. It should be understood that the exterior surface adjustable feature 52 in its enlarged condition could have other desired shape configurations and size dimensions depending on its intended use. As shown in FIG. 1, the exterior surface circumferential dimensions of the enlarged feature 52 are largest toward the distal end 18 of the tube 14. The exterior surface circumferential dimensions of the enlarged feature 52 gradually become smaller as the adjustable feature 52 extends along the portion of the tube length toward the proximal end 16 of the tube 14.

An example of an exterior surface adjustable feature 52 that could be employed on the apparatus 12 is an inflatable balloon having a desired exterior configuration with desired circumferential dimensions when in the enlarged or inflated condition of the balloon, and when deflated the balloon returns to the retracted condition of the feature 52 represented by the solid lines in FIG. 1. The adjustable feature would communicate through one of the lumens 20 through the tube to a manual control 54 to selectively inflate and deflate the adjustable feature 52. As an alternative to an inflatable balloon, the exterior surface adjustable feature 52 could be a mechanical linkage system that enlarges and retracts in the same manner as an inflatable balloon, or other equivalent means of performing the functions of the exterior surface adjustable feature 52.

The apparatus of the invention 12 is also provided with a suction pressure communication feature 62 that communicates through one of the lumens 20 with a manual control 64. The suction feature 62 enables suction pressure to be delivered to a portion or portions of the apparatus tube 14 length in response to the manual operation of the control 64 at the tube proximal end 16. FIG. 1 shows suction holes 62 provided in portions of the apparatus tube 14 length that function as the suction pressure communication feature 62. The holes 62 deliver suction pressure to the exterior surface of the tube 14 length in the areas of the holes 62. In other examples of the apparatus 12, the holes 62 could be replaced by slits in the exterior surface of the tube length or other equivalent means of delivering suction pressure to desired areas of the exterior surface of a tube length. The suction pressure delivered to the holes 62 by manual operation of the control 64 causes the stomach or other hollow viscus organ to contract around the apparatus in the areas of the holes. The portions of the stomach tissue or organ tissue are drawn or wrapped around the exterior surface of the adjustable feature 52 and around the portions of the apparatus tube length having the suction holes 62.

The use of the apparatus of the invention 12 according to the method of the invention is shown in the drawing FIGS. 2-7. In FIGS. 2-7 the apparatus 12 is shown being used as a template or guide in creating a lumen of a desired shape and size in the stomach from the tissue of the stomach. It should be understood that this is only one example of a use of the apparatus and the apparatus is not limited to use in the stomach. The apparatus of the invention 12 is designed to be used as a template or guide for creating a lumen of a desired shape and size in a hollow viscus organ (not necessarily the stomach) from the tissue of the organ.

Figure 2:
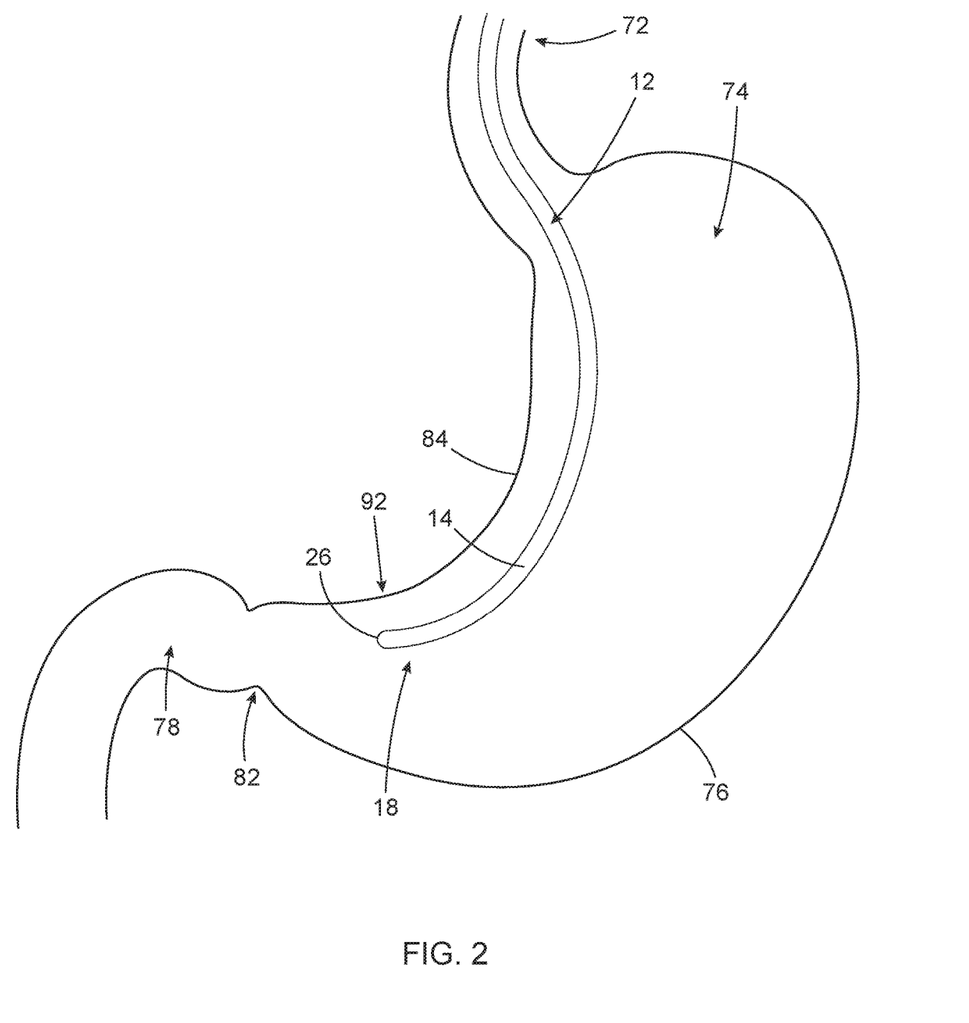
FIG. 2 is a representation of the apparatus being inserted into a hollow viscus organ with the stomach being shown as one example of a hollow viscus organ.

FIG. 2 shows the apparatus 12 being inserted distal end 18 first through the patient's esophagus 72 and into the interior 74 of the patient's stomach 76. As the apparatus 12 is moved through the stomach interior 74 by manually operating the steerable feature control 36, the apparatus distal end 18 is directed toward the pylorus 78 and is inserted through the pyloric valve 82. The illumination light and/or endoscope 28 may be employed in directing the apparatus distal end 18 through the valve. Additionally, the illuminating light of the anchor feature 42 may be used in identifying the location of the apparatus distal end 18 inside the stomach by viewing the light through the stomach wall from the abdominal cavity.

Figure 3:
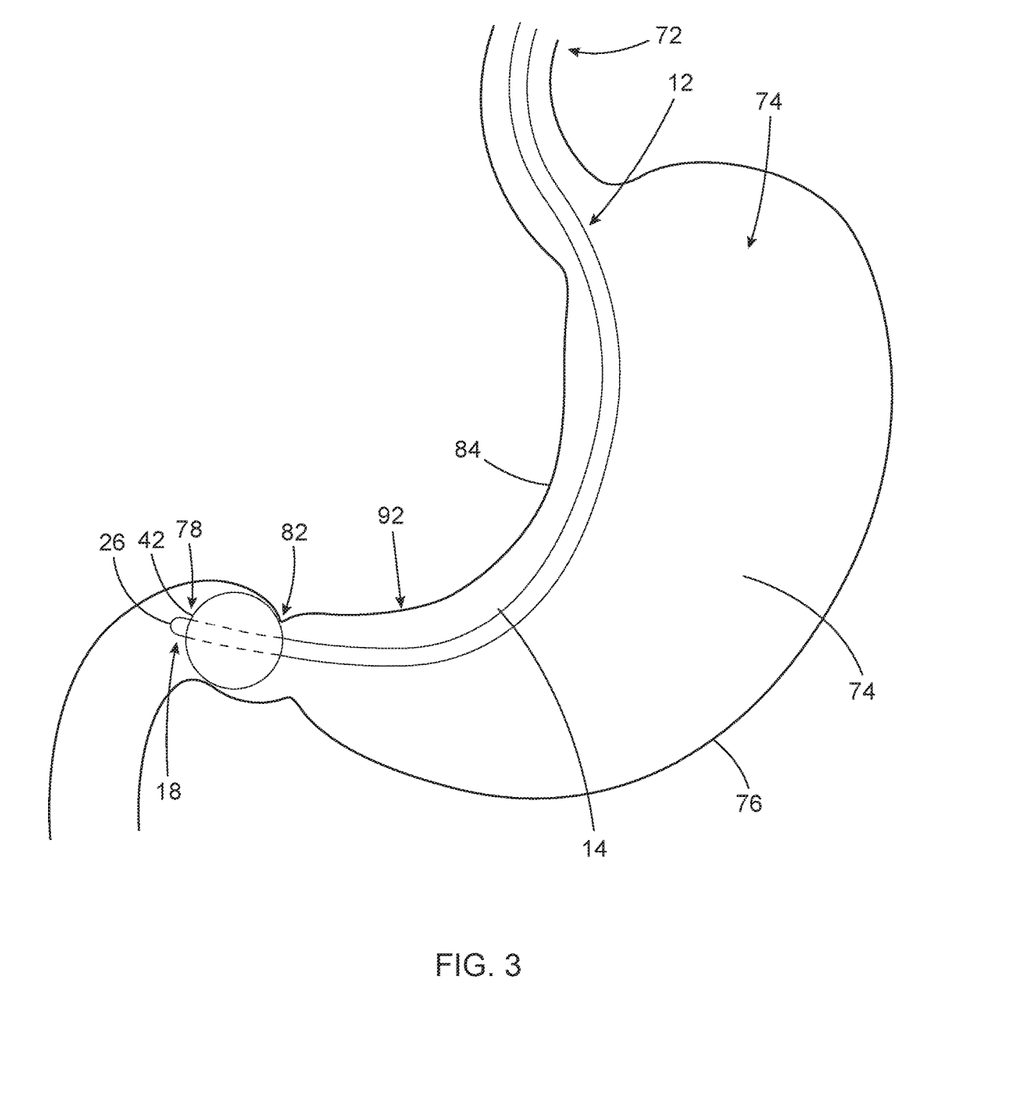
FIG. 3 is a representation of the apparatus being anchored to stomach tissue.

With the apparatus distal end 18 inserted through the pyloric valve 82 and position in the pylorus 78, the anchor feature control 44 is then manually operated to cause the anchor feature 42 to secure the apparatus distal end 18 to the stomach tissue. FIG. 3 shows the balloon anchor feature 42 being inflated in the pylorus 78 and thereby securing the apparatus distal end 18 to the stomach tissue in the pylorus 78.

Figure 4:
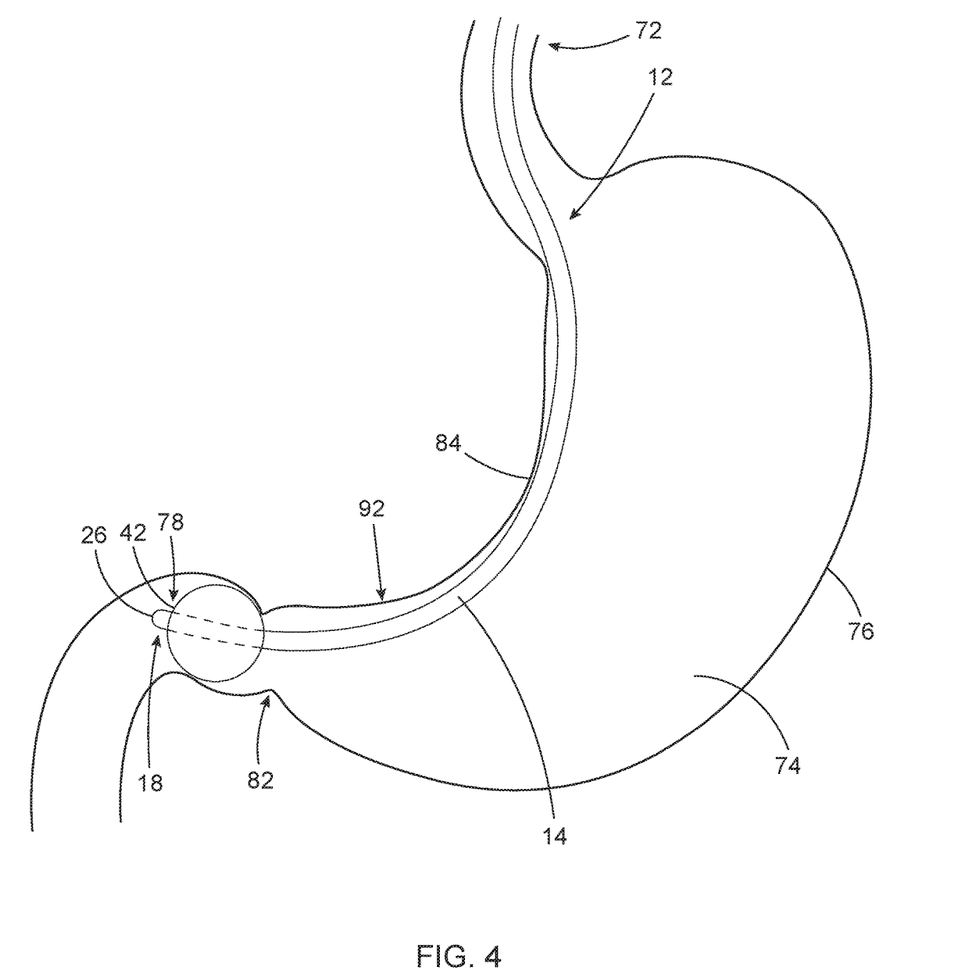
FIG. 4 is a representation of the apparatus being positioned against the lesser curvature of the stomach wall.
Figure 5:
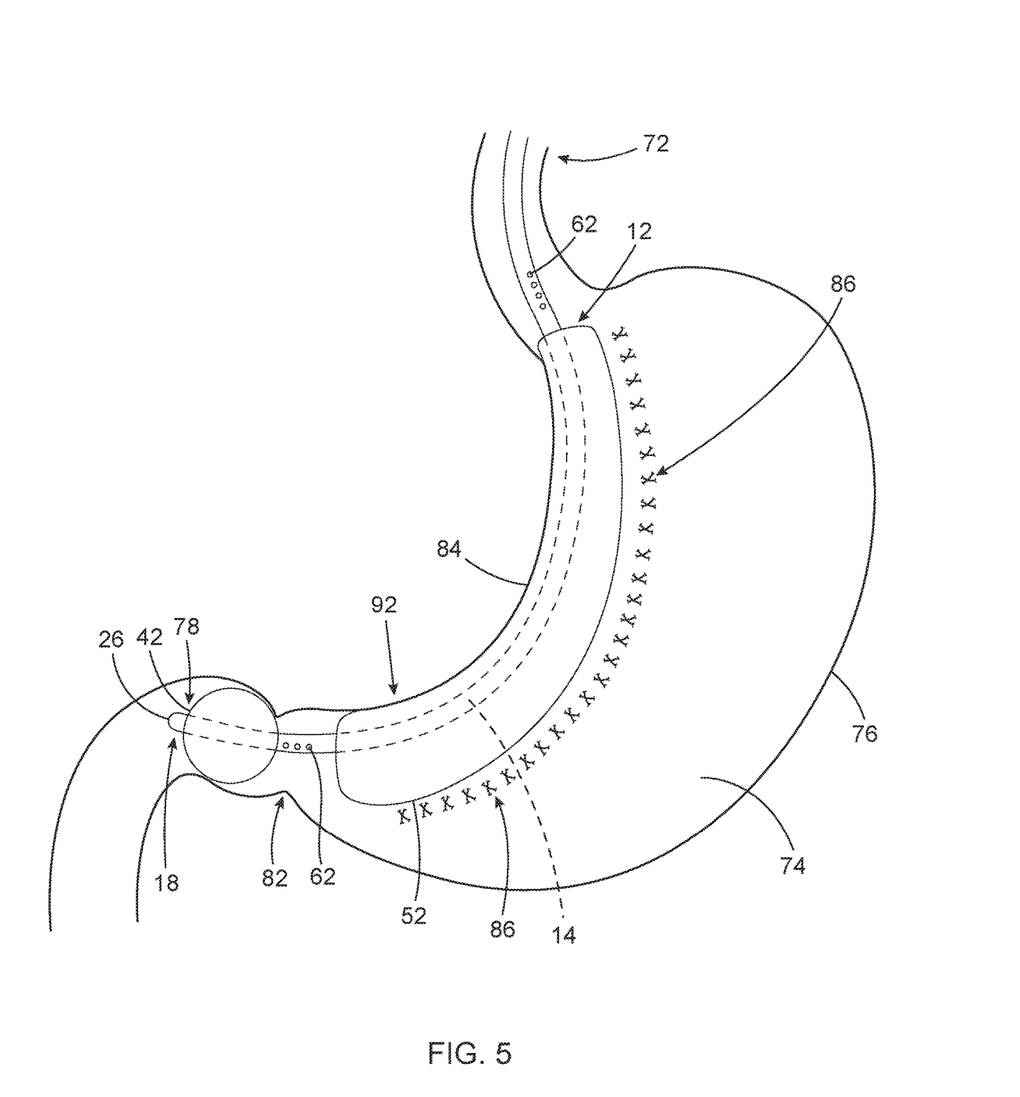
FIG. 5 is a representation of the apparatus in which a portion of the apparatus exterior surface has had its circumferential dimension increased.

The tube 14 of the apparatus 12 is then manipulated from the apparatus proximal end 16 to position a portion of the tube length and in particular to position the external surface adjustment feature 52 against the lesser curvature wall 84 of the stomach 76 as shown in FIG. 4. With the exterior surface adjustment feature 52 so positioned, the control 54 for the feature 52 is then manually operated to cause the feature 52 to enlarge to its desired shape configuration and circumferential dimensions as shown in FIG. 5.

The suction pressure feature 62 of the apparatus 12 is then activated by manual operation of its associated control 64. This evacuates the stomach interior 74 through the suction pressure feature 62 and causes the stomach to contract around the apparatus and in particular around the exterior surface adjustment feature 52. The contraction of the stomach causes portions of the stomach tissue along the stomach lesser curvature 84 to wrap around and envelop the exterior surface adjustment feature 52. With portions of the stomach wall along the lesser curvature 84 wrapped over the exterior surface adjustment feature 52, the template configuration of the exterior surface adjustment feature 52 is demarcated on the stomach wall outside the stomach, making it easier to discern the position of the exterior surface adjustment feature 52 from outside the stomach.

Opposing portions of the stomach wall are then affixed 86 together along the side of the exterior surface adjustment feature 52 that is opposite the stomach lesser curvature 84. The opposing portions of the stomach wall can be affixed 86 together by conventional means such as stapling, suturing, etc. Plication could also be used to reduce the size of the stomach and secure the opposing portions of the stomach wall together along the side of the exterior surface adjustment feature 52 that is opposite the stomach lesser curvature 84. This creates a lumen 88 of a desired shape and size in the stomach from the opposing portions of the stomach wall wrapped around the exterior surface adjustment feature 52. The lumen 88 created has an interior configuration of a desired shape and size that conforms to the shape configuration and the circumferential size dimensions of the exterior surface adjustment feature 52 inside the just created lumen 88. Due to the shape of the adjustment feature 52 and in particular the circumferential dimension of the adjustment feature 52 being larger adjacent the tube distal end 18 and becoming smaller as it extends toward the tube proximal end 16, the interior configuration of the lumen 88 created is without any significant, limiting constriction in the lumen interior in the area of the stomach incisura or other tenuous area of the lumen interior.

Figure 6:
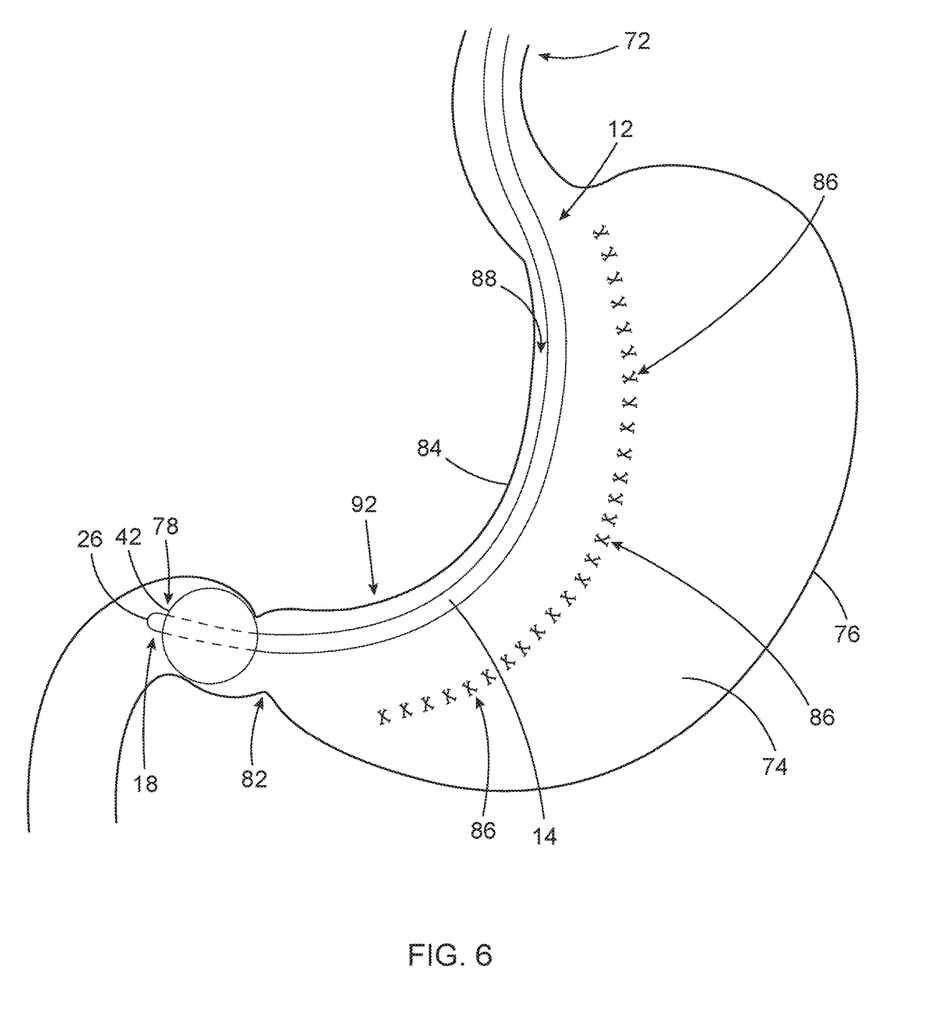
FIG. 6 is a representation of the apparatus functioning as a template in creating a lumen of a desired shape and size in a hollow viscus organ from the tissue of the organ, i.e., in the stomach from the tissue of the stomach.
Figure 7:
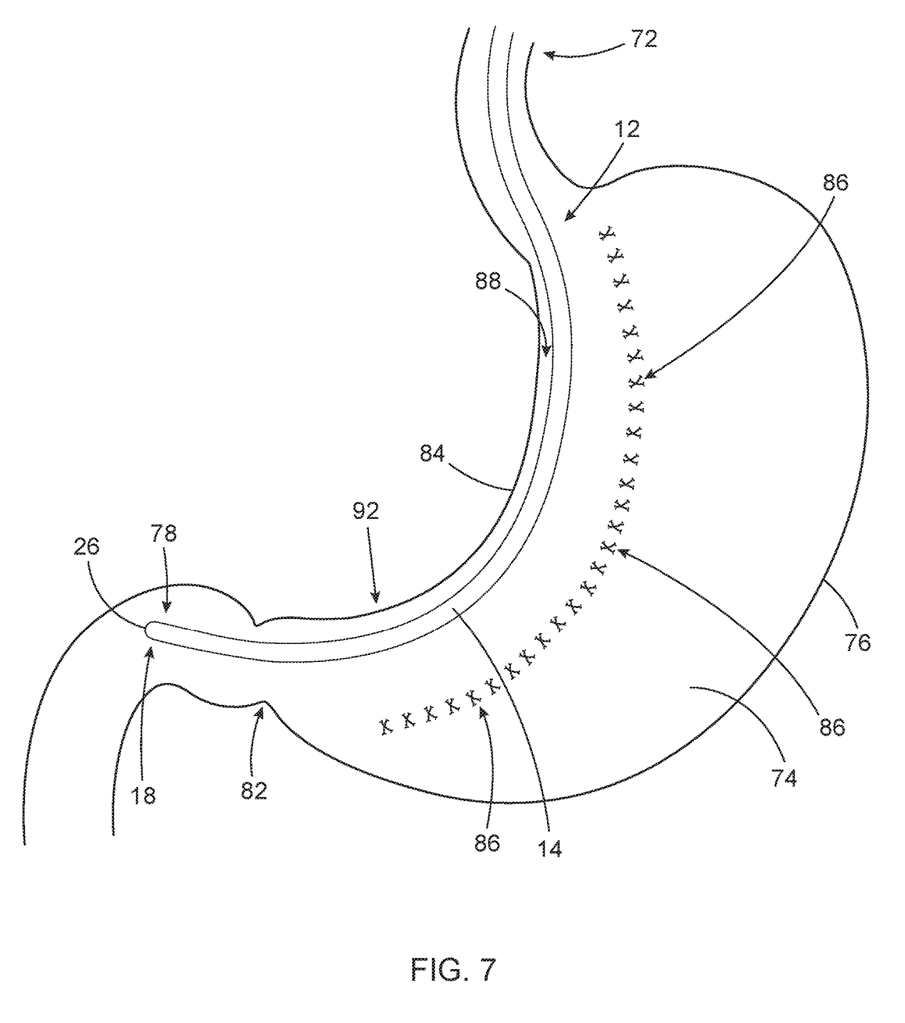
FIG. 7 is a representation of the apparatus after the lumen of the desired shape and size has been created in the stomach and the apparatus is being removed from the stomach.

With the lumen 88 created, the exterior surface adjustment feature 52 is controlled by its associated control 54 to return to its retracted condition on the apparatus tube 14 as shown in FIG. 6. The anchor feature 42 is also controlled by its associated control 44 to disengage from the stomach tissue as shown in FIG. 7. The apparatus 12 can then be removed from the lumen 88. The lumen 88 then functions as a new gastric reservoir with an interior configuration that is without any significant, limiting constriction in the interior configuration of the lumen 88 in the area of the stomach incisura 92 or other tenuous interior area of the created lumen 88 after the apparatus 12 has been removed.

We claim:
1. A method of reducing the size of the stomach of a patient, said method comprising the steps of:
providing a tube having a distal end and a proximal end, with said distal end adapted for insertion into the stomach of the patient;
inserting the distal end of the tube through the patient's esophagus and then into the patient's stomach, and disposing the tube along a lesser curve of the stomach;

demarcating a position of the tube within the stomach so as to make it easily discernable from outside the stomach;

with the tube disposed within the stomach, and the stomach drawn toward the tube, affixing opposing walls of the stomach to each other, along the tube, opposite the lesser curve, performing said affixing step from outside the stomach using the tube as a guide;

withdrawing the tube from the stomach.

2. The method of claim 1, further comprising the step of: drawing the stomach toward the tube prior to the step of affixing opposing walls of the stomach along the tube.

3. The method of claim 2, further comprising the step of: performing the step of drawing the stomach toward the tube by applying suction to the stomach through apertures in the tube.

4. The method of claim 1, further comprising the step of: prior to drawing the stomach toward the tube, anchoring a portion of the distal end of the tube in a pyloric valve of the patient.

5. The method of claim 2, further comprising the step of: prior to drawing the stomach toward the tube, anchoring a portion of the distal end of the tube in a pyloric valve of the patient.

6. The method of claim 3, further comprising the step of: prior to drawing the stomach toward the tube, anchoring a portion of the distal end of the tube in a pyloric valve of the patient.

7. The method of claim 1, further comprising the steps of: providing a balloon about the distal end of the tube, such that the balloon is disposed within the stomach when the distal end of the tube is disposed along the lesser curvature of the stomach; and prior to performing the affixing step, inflating the balloon prior to drawing the stomach toward the tube.

8. The method of claim 1, further comprising the steps of: providing an external surface adjustable feature at the distal end of the tube, such that the external surface adjustable feature is disposed within the stomach when the distal end of the tube is disposed along the lesser curvature of the stomach; and prior to performing the affixing step, expanding the external surface adjustable feature.

9. The method of claim 1, further comprising: performing the step of affixing opposing walls of the stomach by stapling an anterior wall of the stomach and a posterior wall of the stomach together.

10. The method of claim 1, further comprising: performing the step of affixing opposing walls of the stomach by suturing an anterior wall of the stomach and a posterior wall of the stomach together.

11. The method of claim 1, further comprising: illuminating the distal end of the tube with at least one light, while the distal end of the tube is disposed within the stomach.

* * * * *